US006238538B1

United States Patent
Parce et al.

(10) Patent No.: US 6,238,538 B1
(45) Date of Patent: *May 29, 2001

(54) CONTROLLED FLUID TRANSPORT IN MICROFABRICATED POLYMERIC SUBSTRATES

(75) Inventors: John Wallace Parce, Palo Alto; Michael R. Knapp, Aptos, Santa Cruz; Calvin Y. H. Chow, Portola Valley; Luc Bousse, Menlo Park, all of CA (US)

(73) Assignee: Caliper Technologies, Corp., Mountain View, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/287,068

(22) Filed: Apr. 6, 1999

Related U.S. Application Data

(63) Continuation of application No. 09/179,242, filed on Oct. 26, 1998, which is a continuation of application No. 08/843,212, filed on Apr. 14, 1997, now Pat. No. 5,885,470.
(60) Provisional application No. 60/015,498, filed on Apr. 16, 1996, now abandoned.

(51) Int. Cl.[7] .......................................................... B44C 1/22
(52) U.S. Cl. .......................... 204/600; 204/601; 156/500
(58) Field of Search .................................. 204/600, 601; 156/500

(56) References Cited

U.S. PATENT DOCUMENTS

| 4,390,403 | 6/1983 | Batchelder . |
| 4,675,300 | 6/1987 | Zare ..................................... 436/172 |
| 4,908,112 | 3/1990 | Pace . |
| 4,963,498 | 10/1990 | Hillman . |
| 5,126,022 | 6/1992 | Soane . |
| 5,140,161 | 8/1992 | Hillman . |

(List continued on next page.)

FOREIGN PATENT DOCUMENTS

| WO 94/05414 | 3/1994 | (WO) . |
| WO 95/33846 | 12/1995 | (WO) . |
| WO 96/04547 | 2/1996 | (WO) . |
| WO 97/02357 | 1/1997 | (WO) . |
| WO 97/38300 | 10/1997 | (WO) . |
| WO 98/00707 | 1/1998 | (WO) . |
| WO 98/02728 | 1/1998 | (WO) . |
| WO 98/05424 | 2/1998 | (WO) . |

(List continued on next page.)

OTHER PUBLICATIONS

Cohen, C.B. et al., "A Microchip–Based Enzyme Assay for Protein Kinase A," *Anal. Chem.* (1999) 273:89–97.

Jacobson, S.C. et al., "Fused Quartz Substrates for Microchip Electrophoresis," *Anal. Chem.* (1995) 67:2059–2063.

Manz, A. et al., "Electroosmotic pumping and electrophoretic separations for miniaturized chemical analysis systems," *J. Micromech. Microeng.* (1994) 4:257–265.

Ramsey, J.M. et al., "Microfabricated chemical measurement systems," *Nature Med.* (1995) 1:1093–1096.

(List continued on next page.)

*Primary Examiner*—Abun S. Phasge
(74) *Attorney, Agent, or Firm*—Matthew B. Murphy; Stacy Landry; Law Offices of Jonathan Alan Quine

(57) ABSTRACT

Microfluidic devices are provided for the performance of chemical and biochemical analyses, syntheses and detection. The devices of the invention combine precise fluidic control systems with microfabricated polymeric substrates to provide accurate, low cost miniaturized analytical devices that have broad applications in the fields of chemistry, biochemistry, biotechnology, molecular biology and numerous other fields.

31 Claims, 3 Drawing Sheets

U.S. PATENT DOCUMENTS

| | | |
|---|---|---|
| 5,144,139 | 9/1992 | Hillman . |
| 5,164,598 | 11/1992 | Hillman . |
| 5,304,487 | 4/1994 | Wilding . |
| 5,486,335 | 1/1996 | Wilding . |
| 5,498,392 | 3/1996 | Wilding . |
| 5,500,071 | 3/1996 | Kaltenbach . |
| 5,571,410 | 11/1996 | Swedberg . |
| 5,580,523 | 12/1996 | Bard . |
| 5,585,069 | 12/1996 | Zanzucchi et al. . |
| 5,589,136 | 12/1996 | Northrup . |
| 5,593,838 | 1/1997 | Zanzucchi et al. . |
| 5,603,351 | 2/1997 | Cherukuri et al. . |
| 5,632,876 | 5/1997 | Zanzucchi . |
| 5,635,358 | 6/1997 | Wilding . |
| 5,637,469 | 6/1997 | Wilding . |
| 5,639,423 | 6/1997 | Northrup . |
| 5,641,400 | 6/1997 | Kaltenbach . |
| 5,646,039 | 7/1997 | Northup . |
| 5,681,484 * | 10/1997 | Zanzucchi et al. ............ 216/2 |
| 5,699,157 | 12/1997 | Parce . |
| 5,702,618 * | 12/1997 | Saaski et al. ............ 216/2 |
| 5,750,015 | 5/1998 | Soane et al. . |
| 5,779,868 | 7/1998 | Parce et al. . |
| 5,800,690 | 9/1998 | Chow et al. . |
| 5,842,787 | 12/1998 | Kopf-Sill et al. . |
| 5,852,495 | 12/1998 | Parce . |
| 5,858,188 | 1/1999 | Soane et al. . |
| 5,869,004 | 2/1999 | Parce et al. . |
| 5,876,675 | 3/1999 | Kennedy . |
| 5,880,071 | 3/1999 | Parce et al. . |
| 5,882,465 | 3/1999 | McReynolds . |
| 5,885,470 * | 3/1999 | Parce et al. ............ 216/33 |
| 5,942,443 | 8/1999 | Parce et al. . |
| 5,948,227 | 9/1999 | Dubrow . |
| 5,955,028 | 9/1999 | Chow . |
| 5,957,579 | 9/1999 | Kopf-Sill et al. . |
| 5,958,203 | 9/1999 | Parce et al. . |
| 5,958,694 | 9/1999 | Nikiforov . |
| 5,959,291 | 9/1999 | Jensen . |

FOREIGN PATENT DOCUMENTS

| | | |
|---|---|---|
| WO 98/22811 | 5/1998 | (WO) . |
| WO 98/45481 | 10/1998 | (WO) . |
| WO 98/45929 | 10/1998 | (WO) . |
| WO 98/46438 | 10/1998 | (WO) . |
| WO 98/49548 | 11/1998 | (WO) . |
| WO 98/55852 | 12/1998 | (WO) . |
| WO 98/56956 | 12/1998 | (WO) . |
| WO 99/00649 | 1/1999 | (WO) . |
| WO 99/10735 | 3/1999 | (WO) . |
| WO 99/12016 | 3/1999 | (WO) . |
| WO 99/16162 | 4/1999 | (WO) . |
| WO 99/19056 | 4/1999 | (WO) . |
| WO 99/19516 | 4/1999 | (WO) . |
| WO 99/29497 | 6/1999 | (WO) . |

OTHER PUBLICATIONS

Seiler, K. et al., "Planar Glass Chips for Capillary Electrophoresis: Repetitive Sample Injection, Quantitation, and Separation Efficiency," *Anal. Chem.* (1993) 65:1481–1488.

Seiler, K. et al., "Electroosmotic Pumping and Valveless Control of Fluid Flow Within a Manifold of Capillaries on a Glass Chip," *Anal. Chem.* (1994) 66:3485–3491.

Dasgupta et al., Elctroosmosis: A Reliable Fluid Propulsion System for Flow Injection Analysis, Anal. Chem. 66: 1792–1978 (1994).

Polin, For Lab Chips, the Future is Plastic, IVD Technology News, pp. 12, 18, 19 (May/Jun. 1997).

Roberts et al., UV Laser Machined Polymer Substrates for the Development of Microdiagnostic Systems, Anal. chem. 69: 2035–2042 (Jun. 1, 1997).

McCormick et al., Microchannel Electrophoretic Separations of DNA in Injection Molded Plastic Substrates, Anal. Chem. 69:2626–2630 (Jul. 1 1997).

* cited by examiner

CONTROLLED FLUID TRANSPORT IN MICROFABRICATED POLYMERIC SUBSTRATES

CROSS REFERENCE TO RELATED APPLICATIONS

This application is a continuation and claims the benefit of U.S. application Ser. No. 09/179,242, filed Oct. 26, 1998 which is a continuation of U.S. Ser. No. 08/843,212, filed Apr. 14, 1997 (now issued U.S. Pat. No. 5,885,470) which is a CIP of Ser. No. 60/015,498, filed Apr. 16, 1996 (now abandoned), the disclosures of which are incorporated by reference.

This application is a regular application of provisional Patent Application Ser. No. 60/015,498, filed Apr. 16, 1996, which is hereby incorporated herein by reference in its entirety for all purposes.

BACKGROUND OF THE INVENTION

There has recently been an increasing interest in the application of manufacturing techniques common to the electronics industry, such as photolithography, wet chemical etching, etc., to the microfabrication of fluidic devices for use in obtaining chemical and biochemical information.

The manufacture of fluidic devices in solid substrates, e.g., silicon, glass, etc., was described as early as 1979, with the disclosure of the Stanford Gas Chromatograph (discussed in Manz et al., Avd. in Chromatog. (1993) 33:1–66, citing Terry et al., IEEE Trans. Electron. Devices (1979) ED-26:1880). These fabrication technologies have since been applied to the production of more complex devices for a wider variety of applications.

To date, the most prominent use of this technology has been in the area of capillary electrophoresis (CE). Capillary electrophoresis typically involves the injection of a macromolecule containing sample, e.g., nucleic acids or proteins, into one end of a thin capillary. A potential is then applied along the length of the capillary to electrophoretically draw the materials contained within the sample through the channel. The macromolecules present in the sample then separate from each other based upon differences in their electrophoretic mobility within the capillary. Such differences in electrophoretic mobility typically result from differences in the charge and/or size of a compound. Other factors can also affect the electrophoretic mobility of a given compound, such as interactions between the compound and the capillary walls, interactions with other compounds, conformation of the compound, and the like.

Capillary electrophoresis methods have traditionally employed fused silica capillaries for the performance of these electrophoretic separations. In more recent applications, this fused silica capillary has been replaced by an etched channel in a solid planar substrate, e.g., a glass or silica slide or substrate. A covering layer or substrate provides the last wall of the capillary.

Early discussions of the use of this planar substrate technology for fabrication of such devices are provided in Manz et al., Trends in Anal. Chem. (1990) 10(5):144–149 and Manz et al., Adv. in Chromatog. (1993) 33:1–66, which describe the fabrication of fluidic devices and particularly capillary electrophoresis devices, in silicon and glass substrates.

Although generally concerned with the movement of material in small scale channels, as the name implies, capillary electrophoresis methods employ electrophoresis to affect that material movement, e.g., the movement of charged species when subjected to an electric field. While providing significant improvements in the separation of materials, these capillary electrophoresis methods cannot be used in the direction of bulk materials or fluids within microscale systems. In particular, because electrophoresis is the force which drives the movement of materials in CE systems, species within the material to be moved which have different electrophoretic mobilities will move at different rates. This results in a separation of the constituent elements of the material. While this typically is not a problem in CE applications, where separation is the ultimate goal, where the goal is the bulk transport of fluid borne materials from one location to another, electrophoretic separation of the constituent elements of that material can create numerous problems. Such problems include excessive dilution of materials in order to ensure complete transport of all materials, biasing of a transported material in favor if faster electrophoresing species and against slower or even oppositely electrophoresing species.

While mechanical fluid direction systems have been discussed for moving and directing fluids within microscale devices, e.g., utilizing external pressures or internal microfabricated pumps and valves, these methods generally require the use of costly microfabrication methods, and/or bulky and expensive equipment external to the microfluidic systems. Accordingly, it would generally be desirable to produce a microscale fluidic device that can be easily and cheaply manufactured. The present invention meets these and other needs.

SUMMARY OF THE INVENTION

It is a general object of the invention to provide microfluidic devices for the performance of chemical and biochemical analyses, syntheses and detection. The devices of the invention combine precise fluidic control systems with microfabricated polymeric substrates to provide accurate, low cost, miniaturized analytical devices that have broad applications in the fields of chemistry, biochemistry, biotechnology, molecular biology and numerous other fields.

In a first aspect, the present invention provides a microfluidic system which includes a microfluidic device. The device comprises a body that is substantially fabricated from a polymeric material. The body includes at least two intersecting channels disposed therein, where the interior surfaces of these channels have a surface potential associated therewith, which is capable of supporting sufficient electroosmotic mobility of a fluid disposed within the channels. At least one of the two intersecting channels has at least one cross sectional dimension in the range of from about 0.1 $\mu$m to about 500 $\mu$m. The device also includes at least first, second and third ports disposed at termini of the first channel and at least one terminus of the second channel, and these ports are in electrical contact with fluid in the channels. The system also includes an electrical control system for concomitantly applying a voltage at the three ports, to selectively direct flow of a fluid within the intersecting channels by electroosmotic flow.

The present invention also provides a method of fabricating microfluidic devices for use with an electroosmotic fluid direction system. The method comprises molding a polymeric material to form a substrate that has at least one surface, and at least first and second intersecting channels disposed in that surface. Each of the at least first and second intersecting channels has an interior surface which has a surface potential associated therewith, which is capable of supporting sufficient electroosmotic flow of a fluid in those channels. Again, at least one of the intersecting channels has at least one cross-sectional dimension in the range of from about 0.1 μm to about 500 μm. A cover layer is overlaid on the surface of the substrate, whereby the cover layer encloses the intersecting channels. Together, the substrate and cover layer will also comprise at least three ports disposed therein, each of the at least three ports being in fluid communication with first and second termini of said first channel and at least one terminus of the second channel.

In a related aspect, the present invention also provides a method for directing movement of a fluid within a microfluidic device. The method comprises providing a microfluidic device having at least first and second intersecting channels disposed therein. Each of the first and second intersecting channels has a fluid disposed therein, wherein the at least first and second channels have interior surfaces having a surface potential associated therewith, which is capable of supporting sufficient electroosmotic mobility of the fluid disposed in those channels. The device also includes at least first, second, third and fourth ports disposed in the substrate, wherein the first and second ports are in fluid communication with the first channel on different sides of the intersection of the first channel with the second channel, and the third and fourth ports are in fluid communication with the second channel on different sides of the intersection of the second channel with the first channel. A voltage gradient is then applied between at least two of the first, second, third and fourth ports to affect movement of said fluid in at least one of the first and second intersecting channels.

DETAILED DESCRIPTION OF THE INVENTION

The present invention generally provides microfluidic devices and systems, as well as methods for using such devices and systems. The devices and systems of the present invention are generally characterized in that they typically include precise fluid direction and control systems, and that they are largely fabricated from polymeric materials. These two characteristics provide the microfluidic devices and systems of the present invention with a number of advantages over previously used materials, such as silica based substrates, semiconductor substrates, e.g., silicon, and the like, including ease of manufacturing, low cost of materials, and inertness to a wide range of potential reaction conditions, including salts, pH and application of electric fields. In addition, these devices and systems also are generally characterized by their inclusion of, or adaptability to precise fluid direction and control elements.

I. Microfluidics, Generally

As noted above, the present invention generally relates to microfluidic devices and systems, which include precise fluid control elements, e.g., fluid transport and direction systems, and which are fabricated from polymeric substrates.

The term "microfluidic device" as used herein, refers to a device or aggregation of devices, which includes a plurality of interconnected channels or chambers, through which materials, and particularly fluid borne materials may be transported to effect one or more preparative or analytical manipulations on those materials. Typically, such channels or chambers will include at least one cross sectional dimension that is in the range of from about 0.1 μm to about 500 μm, and preferably from about 1 μm to about 100 μm. Dimensions may also range from about 5 μm to about 100 μm Use of dimensions of this order allows the incorporation of a greater number of channels, chambers or sample wells in a smaller area, and utilizes smaller volumes of reagents, samples and other fluids for performing the preparative or analytical manipulation of the sample that is desired.

Figure 1:
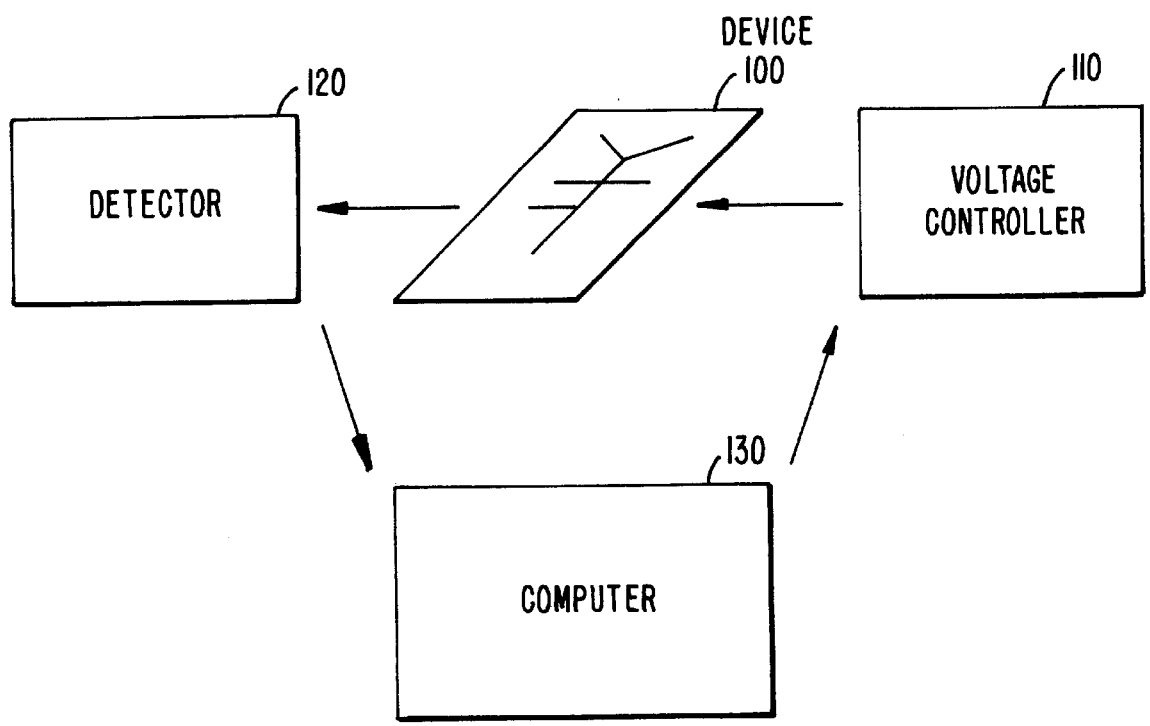
FIG. 1 shows a schematic illustration of one embodiment of a microfluidic system.

The microfluidic device may exist alone or may be a part of a microfluidic system which can include: sampling systems for introducing fluids, e.g., samples, reagents, buffers and the like, into the device; detection systems; data storage systems; and control systems, for controlling fluid transport and direction within the device, monitoring and controlling environmental conditions to which the fluids in the device are subjected, e.g., temperature, current and the like. A schematic illustration of one embodiment of such a system is shown in FIG. 1. As shown, the system includes a microfluidic device 100. The device, and particularly the reagent wells or ports of the device are electrically connected to voltage controller 110, which controls fluid transport within the device. An example of a particularly preferred voltage controller is described in, e.g., U.S. patent application Ser. No. 08/691,632, filed Aug. 2, 1996, and incorpoated herein by reference in its entirety for all purposes. Detection of the output of the device is carried out by detector 120. Both detector 120 and voltage controller 110 are connected to computer 130, which instructs voltage controller in the selective application of varying voltage levels to the various ports of the device 100. The computer also receives and stores detection data from detector 120, and is typically appropriately programmed to perform analysis of those data.

Microfabricated fluidic substrates have been described for the performance of a number of analytical reactions. For example, U.S. Pat. No. 5,498,392 to Wilding and Kricka, describes a mesoscale apparatus which includes microfabricated fluid channels and chambers in a solid substrate for the performance of nucleic acid amplification reactions. Further, U.S. Pat. No. 5,304,487 to Wilding and Kricka also describes a mesoscale device for detecting an analyte in a sample which device includes a cell handling region. The device also includes microfabricated channels and chambers having at least one cross-sectional dimension in the range of from 0.1 μm to about 500 μm. Similar devices are also described in U.S. Pat. Nos. 5,296,375, 5,304,487, 5,427,946, and 5,486,335, also to Wilding and Kricka, for detection of cell motility and fluid characteristics, e.g., flow restriction as a function of analyte concentration. The disclosure of each of these patents is incorporated herein by reference.

III. Polymeric Substrates

Typically, fabrication of fluidic systems having small or even microscale dimensions has drawn on techniques that are widely used in the electronics industry, such as photolithography, wet chemical etching, controlled vapor deposition, laser drilling, and the like. As a result, these microfabricated systems have typically been manufactured from materials that are compatible with these manufacturing techniques, such as silica, silicon, gallium arsenide and the like. While each of these materials is well suited for microfabrication, and many are well suited for inclusion in microfluidic systems, the costs associated with the materials and manufacture of devices utilizing such materials renders that use commercially impractical.

The present invention on the other hand, is characterized in that the devices are substantially fabricated from polymeric materials. By "Polymeric Substrates" or "Polymeric Materials" is generally meant organic, e.g., hydrocarbon based, polymers that are capable of forming rigid or semi-rigid structures or substrates. By "substantially fabricated from polymeric materials" is meant that greater than 50% (w/w) of the materials used to manufacture the microfluidic devices described herein are polymeric materials. For example, while a substrate may be fabricated entirely of a polymeric material, that substrate may also include other non-polymeric elements incorporated therein, including, e.g., electrodes, glass or quartz detection windows, glass cover layers and the like. Typically, the devices of the present invention comprise greater than 60% polymeric materials, preferably greater than 70%, more preferably greater than 80% and often greater than 95% polymeric materials.

Microfabrication of polymeric substrates for use in the devices of the invention may be carried out by a variety of well known methods. In particular, polymeric substrates may be prepared using manufacturing methods that are common in the microfabrication industry, such as injection molding or stamp molding/embossing methods where a polymeric substrate is pressed against an appropriate mold to emboss the surface of the substrate with the appropriate channel structures. Utilizing these methods, large numbers of substrates may be produced using, e.g., rolling presses or stamps, to produce large sheets of substrates. Typically, these methods utilize molds or stamps that are themselves, fabricated using the above-described, or related microfabrication techniques.

Although generally not preferred for the manufacture of polymeric substrates for cost reasons, other microfabrication techniques are also suitable for preparation of polymeric substrates, including, e.g., laser drilling, etching techniques, and photolithographic techniques. Such photolithographic methods generally involve exposing the polymeric substrate through an appropriate photolithographic mask, i.e., representing the desired pattern of channels and chambers, to a degradative level of radiation, e.g., UV light for set periods of time. The exposure then results in degradation of portions of the surface of the substrate resulting in the formation of indentations which correspond to the channels and/or chambers of the device.

Suitable polymeric materials for use in fabricating substrates are generally selected based upon their compatibility with the conditions present in the particular operation to be performed by the device. Such conditions can include extremes of pH, temperature and salt concentration. Additionally, substrate materials are also selected for their inertness to critical components of an analysis or synthesis to be carried out by the device, e.g., proteins, nucleic acids and the like.

Polymeric substrate materials may be rigid, semi-rigid, or non-rigid, opaque, semi-opaque or transparent, depending upon the use for which they are intended. For example, devices which include an optical or visual detection element, e.g., for use in fluorescence based or calorimetric assays, will generally be fabricated, at least in part, from a transparent polymeric material to facilitate that detection. Alternatively, transparent windows of, e.g., glass or quartz, may be incorporated into the device to allow for these detection elements. Additionally, the polymeric materials may have linear or branched backbones, and may be cross-linked or non-cross-linked. Examples of preferred polymeric materials include, e.g., polydimethylsiloxanes (PDMS), polymethylmethacrylate (PMMA), polyurethane, polyvinylchloride (PVC), polystyrene, polysulfone, polycarbonate and the like.

Typically, the polymeric substrates used in the devices of the present invention are fabricated in two or more parts. Specifically, a first planar substrate element is provided having a plurality of grooves and/or wells, corresponding to the fluid channels and/or chambers, manufactured, e.g., molded or machined, into one of its planar surfaces. These grooves provide the bottom and side walls of the channels and chambers of the devices. A second planar substrate element is then mated with the first to define the top wall of the channels and chambers. The two members are bonded together in order to ensure that the channels and chambers in the substrate are fluid tight. Bonding of the two members may be accomplished by a number of methods that are known in the art, such as through the use of adhesives, e.g., UV curable adhesives, or by sonically welding one member to the other, e.g., as described in Published PCT Application No. WO 95/12608, which is incorporated herein by reference in its entirety for all purposes. Alternatively, the two planar elements may be bonded by applying pressure to the joined pair under elevated temperatures, sufficient to bond the two planar elements together.

As described above, the polymeric substrate may be rigid, semi-rigid, nonrigid or a combination of rigid and nonrigid elements, depending upon the particular application for which the device is to be used. In one particular embodiment, a substrate is made up of at least one softer, flexible substrate element and at least one harder, more rigid substrate element, one of which includes the channels and chambers manufactured into its surface. Upon mating the two substrates, the natural adhesion of the soft, less rigid substrate, either to another less rigid substrate or to a more rigid substrate, allows formation of an effective fluid seal for the channels and chambers, obviating the difficulties associated with gluing or melting more rigid plastic components together.

III. Fluid Direction System

The devices of the present invention, in addition to being largely fabricated from polymeric substrates, also are generally characterized by the use of fluid transport and direction systems that do not employ mechanical pumps or valves, or the application of external pressure to selectively move and direct the fluids through the various channels or chambers contained in the device or system. Instead, the microfluidic devices and systems of the present invention typically utilize controlled electroosmotic flow to transport and selectively direct fluids among and through the interconnected series of channels contained within the device. One example of such controlled electroosmotic flow is described in published International Patent Application No. WO 96/04547 to Ramsey, which is incorporated herein by reference in its entirety for all purposes.

In brief, when an appropriate fluid is placed in a channel or other fluid conduit having functional groups present at the surface, those groups can ionize. For example, where the surface of the channel includes hydroxyl functional groups at the surface, i.e., as in the case of silica, protons can leave the surface of the channel and enter the fluid. Under such conditions, the surface will possess a net negative charge, whereas the fluid will possess an excess of protons or positive charge particularly localized near the interface between the channel surface and the fluid. By applying an electric field across the length of the channel, cations will flow toward the negative electrode. Movement of the positively charged species in the fluid pulls the solvent with them. The steady state velocity of this fluid movement in the channel is directly proportional to the zeta potential of the surface that is in contact with the fluid being moved (See, e.g., Published International Application No. WO. 96/04547, previously incorporated herein).

Fluid velocity within a channel is also generally given as:

$$v=(\mu EO)E$$

Where v is the velocity of the fluid, $\mu EO$ is the electroosmotic mobility of the fluid in the system, and E is the electric field strength. Thus, the electroosmotic mobility of the fluid is also directly proportional to the zeta potential of the surface that is contacting the fluid.

The fluid flow rate, or volume velocity, within a specific channel (Q) is then given as:

$$Q=(\mu EO)EA$$

where $\mu EO$ and E are as defined above, Q is the volume velocity of the fluid and A is the cross sectional area of the channel through which the fluid is flowing. Using the above equations, therefore, one can calculate the electroosmotic mobility of a given fluid in a given channel from either its velocity or its volumetric flow rate, e.g., in $cm^3$/second.

Accordingly, the electroosmotic fluid control systems employed in the devices of the present invention generally require channels having surfaces with sufficient zeta potentials to propagate an acceptable level of electroosmotic mobility within those channels.

This zeta potential requirement, in combination with the availability of suitable manufacturing techniques as described above, has resulted in silica substrates generally being employed for systems utilizing such electroosmotic flow. Optimized planar silica substrates having channels fabricated into their surfaces, have generally supported an electroosmotic mobility of approximately $5 \times 10^{-4}$ $cm^2V^{-1}s^{-1}$ for a 5 mM Sodium borate buffer at pH 7, that is disposed within those channels.

However, as noted above, the devices and systems of the present invention utilize polymeric substrates. In general, such polymeric materials generally have hydrophobic surfaces and will have relatively low surface potentials, generally making them less suitable for electroosmotic flow systems.

Accordingly, incorporation of the electroosmotic fluid control systems described above, into the polymeric substrates used in the present invention, typically requires either: (1) selection of a polymeric material which has a surface potential capable of supporting sufficient electroosmotic mobility of a fluid disposed in contact with that surface; or (2) modification of the surfaces of the polymeric substrate that are to be in contact with fluids, to provide a surface potential that is capable of supporting sufficient electroosmotic mobility. As used herein, the phrase "support sufficient electroosmotic mobility" means that the surfaces in contact with the fluid, e.g., the walls of a channel, possess a sufficient zeta potential, whereby those surfaces or channel walls are capable of supporting an electroosmotic mobility ($\mu EO$) of at least about $1 \times 10^{-5}$ $cm^2V^{-1}s^{-1}$, for a buffer when that buffer is in contact with those walls, e.g., disposed within those channels, e.g., a buffer of from about 1 mM to about 100 mM sodium borate at a pH of from about 6 to about 9. For the purposes of the present invention, $\mu EO$ is referred to in terms of a standard buffer of from about 1 mM to about 10 mM sodium borate buffer, at a pH of from about 7 to about 9, for example, 5 mM sodium borate, pH 7. In preferred aspects, the surfaces in contact with the fluid are capable of supporting a $\mu EO$ under the above conditions, of at least about $2 \times 10^{-5}$ $cm^2V^{-1}s^{-1}$, preferably, at least about $5 \times 10^{-5}$ $cm^2V^{-1}s^{-1}$, and in particularly preferred aspects, at least about $1 \times 10^{-4}$ $cm^2V^{-1}s^{-1}$.

Although the above listed polymeric materials possess sufficient surface potential to support sufficient electroosmotic mobility of fluids in contact therewith, in the case of many polymeric materials, the surface potential is so low that it does not support sufficient electroosmotic mobility, as defined above. As such, systems that employ these polymeric materials, without modification, are largely commercially impractical for use in microfluidic devices, due to the extremely slow rates attainable for fluid transport.

Accordingly, in particularly preferred aspects, the surfaces of the polymeric material that are to be in contact with the fluids of interest, and thus contributing and supporting E/O mobility, are subjected to modification to effectively increase the zeta potential of those surfaces, and thus improve E/O mobility achievable within devices fabricated from these materials.

Surface modification of polymeric substrates may take on a variety of different forms, including coating those surface with an appropriately charged material, derivatizing molecules present on the surface to yield charged groups on that surface, and/or coupling charged compounds to the surface.

One example of an embodiment employing a surface coating method involves using a polymeric substrate which includes a surface that comprises a fluorocarbon polymer, e.g., polytetrafluoroethylene (Teflon), which on its own has a very low surface potential. The substrate may be fabricated in whole or in part from the fluorocarbon polymer, or alternatively, the polymer may be applied as a coating on a polymeric substrate of a different composition.

The surfaces of the substrate that are to be in contact with the fluid are then treated with charged, fluorinated modifier compounds, commercially available from, e.g., J & W Scientific (Folsom, Calif.). These fluorinated modifier compounds interact with the fluorocarbon polymer surface of the substrate to present charged functional groups at that surface. These modifiers are available in anionic or cationic forms.

The coating of the surfaces that are intended to contact the fluids within the device may be performed on the assembled microfluidic device, e.g., by pumping the perfluoronated compounds through the channels and/or chambers of the device. Alternatively, the entire surface of the substrate, including the surfaces of the channels and chambers, may be subjected to treatment, e.g., by immersion in or deposition of these compounds on that surface.

In a related aspect, detergents with their charged head groups and hydrophobic tails, function as particularly desirable coating materials. Upon passing such materials through the channels of the system, the hydrophobic tails of the detergent will localize to the hydrophobic surface of the substrate, thereby presenting the charged head group to the fluid layer, creating a charged surface. More particularly, preparation of a charged surface on the substrate involves the exposure of the surface to be modified, e.g., the channels and/or reaction chambers, to an appropriate solvent which partially dissolves or softens the surface of the polymeric substrate. Selection of appropriate solvents will generally depend upon the polymeric material that is used for the substrate. For example, chlorinated hydrocarbon solvents, i.e., trichloroethane (TCE), dichloroethane and the like, are particularly useful as solvents for use with PMMA and polycarbonate polymers.

A detergent solution is then contacted with the partially dissolved surface, whereby the hydrophobic portion of the detergent molecules will associate with the partially dissolve polymer. A wide variety of detergents may be used in this method, and are generally selected based upon their compatibility with the ultimate end use of the microfluidic device or system, including without limitation, for example, SDS (sodium dodecyl sulfate), DTAB (dodecyltrimethylammonium bromide), or CTAB (cetyltrimethylammoniumbromide). Following contacting the polymer with the appropriate detergent, the solvent is then washed from the surface, e.g., using water, whereupon the polymer surface hardens with the detergent embedded into the surface, presenting the charged head group to the fluid interface.

Differentially charged areas may be selected and prepared using a photolyzable detergent, which photolyzes to produce a positively or negatively charged group. Irradiation of selected areas on the substrate surface then fields these charged groups in these areas.

In alternative aspects, the polymeric materials, either as the substrate, or as a coating on the substrate, may themselves be modified, derivatized, etc., to present an appropriate zeta potential at the fluid interface.

For example, once a polymeric material has been molded or otherwise fabricated into a substrate as described herein, the surfaces of that substrate may be modified or activated, e.g., by oxygen plasma irradiation of those surfaces. Polydimethylsiloxane (PDMS), for example, may be modified by plasma irradiation, which oxidizes the methyl groups present in the polymer, liberating the carbon atoms and leaving hydroxyl groups in their place. This modification effectively creates a glass-like surface on the polymeric material, with its associated hydroxyl functional groups. As noted above, this type of surface is well suited for propagation of electroosmotic mobility of fluids.

In an alternate but related aspect, block copolymers may be used in combination with the polymer of interest, to present an appropriate surface for the device. For example, polytetrafluoroethylene/polyurethane block copolymer may be mixed with a polyurethane polymer prior to molding the substrate. The immiscibility of the polytetrafluoroethylene portion of the copolymer in the polyurethane results in that copolymer localizing at the surface of the polyurethane substrate. This surface can then be treated as described above, e.g., using fluorinated buffer modifiers.

IV. Microfluidic Devices

As noted above, the devices and systems of the present invention are characterized in that they are fabricated largely from polymeric substrates, and in that they employ controlled electroosmotic flow in selectively transporting and directing fluids through interconnected channels and/or chambers, that are contained within these microfluidic systems. By "selectively transporting and directing" is meant the transporting of fluids through miroscale or microfluidic channels, and the selective direction, e.g., dispensing, aliquoting or valving, of discrete quantities of those fluids among interconnected channels, e.g., from one channel to another.

Accordingly, in preferred aspects, the devices and systems of the invention generally comprise a body having at least two intersecting channels disposed within it, which body is fabricated, at least in-part, from a polymeric material. Typically, the body includes a polymeric substrate having the intersecting channels fabricated into a substantially flat surface of the substrate as grooves. A cover is then overlaid on this surface to seal the grooves and thereby form the channels.

In order to effectively and accurately control fluid direction in intersecting channel structures, the fluid direction systems used in the devices and systems of the present invention typically include a plurality of ports or reservoirs that are in electrical contact and typically in fluid communication with the channels on different sides of the various intersections. Typically, such ports are placed at and in electrical contact with the free termini of the intersecting channels. By "free terming" or "free terminus" is generally meant that a particular terminus of a channel is not the result of an intersection between that channel and another channel. Often such ports comprise holes disposed through the cover layer which overlays the first substrate, thereby forming wells or reservoirs at these channel termini.

These ports generally provide an access for electrodes to be placed in contact with fluids contained within the channels, as well as Providing an access for introducing fluids, and reservoirs for storing fluids in the devices.

Although they can exist as part of a separate device employed in an overall microfluidic system, a number of additional elements may be added to the polymeric substrate to provide for the electroosmotic fluid control systems. These elements may be added either during the substrate formation process, i.e., during the molding or stamping steps, or they may be added during a separate, subsequent manufacturing step. These elements typically include electrodes for the application of voltages to the various fluid reservoirs, and in some embodiments, voltage sensors at the various channel intersections to monitor the voltage applied.

Where electrodes are included as an integrated element of the microfluidic device, they may be incorporated during the molding process, i.e., by patterning the electrodes within the mold so that upon introduction of the polymeric material into the mold, the electrodes will be appropriately placed and fixed within the substrate. Alternatively, the electrodes and other elements may be added after the substrate is formed, using well known microfabrication methods, e.g., sputtering or controlled vapor deposition methods followed by chemical etching, and the like.

In operation, the materials stored in the reservoirs are transported electroosmotically through the channel system, delivering appropriate volumes of the various materials to one or more regions on the substrate in order to carry out a desired analysis or synthesis.

To provide such controlled electroosmotic flow, the microfluidic system includes a voltage controller electrically connected to electrodes placed or fabricated into the various reagent wells on the device. The voltage controller is capable of applying selectable voltage levels, to each of the ports or reservoirs, including ground. Such a voltage controller can be implemented using multiple voltage dividers and multiple relays to obtain the selectable voltage levels desired. Typically, the voltage controller is interfaced with a computer or other processor, e.g., a PC compatible Pentium microprocessor based or Macintosh Power PC computer, which is programmed to instruct appropriate application of voltages to the various electrodes.

In operation, fluid transport within these devices is carried out by applying a voltage gradient along the path of desired fluid flow, thereby electroosmotically driving fluid flow along that path. Some methods for affecting electroosmotic fluid flow incorporate a "floating port" fluid direction system, where a sample fluid in one reservoir and channel is drawn across the intersection of that channel with another channel, by applying a voltage gradient along the length of the first channel, i.e., by concomitantly applying a voltage to the two ports at the ends of the first channel. Meanwhile, the two ports at the ends of the second channel are allowed to "float," i.e., no voltage is applied. The plug of sample fluid at the intersection is then drawn into the second channel by applying a potential to the electrodes at each end of the second channel. While this method allows injection of a sample of one fluid into a different channel, a number of disadvantages remain. In particular, leakage can occur at the sample intersection as a result of fluid convection, e.g., fluid from one channel "bleeds over" into the other channel. This bleeding over effect can result in imprecise and nonreproducible fluid movements, which can be problematic where one desires more precise fluid control.

However, in preferred aspects, the fluid control and direction systems incorporated into the systems of the present invention apply voltages to multiple reservoirs, simultaneously. In the case of a fluid being transported in a first channel through an intersection with a second channel, this permits the introduction of constraining or directing flows from the second channel, whereby one can precisely control the level of fluid flow in a given direction. This simultaneous application of potential to multiple ports allows for specific control of the fluid at the intersection of the channels, reducing or eliminating the convective effects that are generally seen with floating port methods. For example, a fluid of interest flowing through an intersection of two channels may be precisely constrained by flowing additional fluids from the side channels by appropriate, simultaneous application of voltages to the reservoirs or ports at the ends of those channels, resulting in the fluid of interest being maintained in a "pinched" conformation which prevents bleeding over into the side channels. The volume of the fluid of interest contained within the intersection is readily calculable based upon the volume of the intersection, and also is readily reproducible. Further, this volume of fluid can be readily diverted to one of the intersecting channels by appropriate modulation of the potentials applied at each reservoir or port.

In a related aspect, fluid flow in a first channel past an intersection with a second channel may be "gated" or "valved" by fluid flow in the second channel through that intersection. Although described in terms of a valve, it will be readily apparent that fluid direction using these methods requires no actual mechanical valve, but instead relies upon application of electrical forces through the intersection.

By opening and closing the "valve" through appropriate switching of voltage applied to the reservoirs, one can effectively meter the amount of fluid flowing in the first channel past the intersection. Both pinched and gated control systems are described in significant detail in published International Application No. WO 96/04547, previously incorporated by reference.

In addition to these pinched and gated flow systems, application the simultaneous application of voltages at multiple, e.g., three or more ports, permits controlled fluid flow in more complex interconnected channel structures. For example, in flowing of fluids through interconnected parallel channels, voltages may be applied to multiple reservoirs in order to drive simultaneous flow in the parallel channels without the generation of transverse electric fields which can effectively short circuit the system.

As alluded to above, incorporation of these electroosmotic flow systems into the microfluidic devices and systems of the present invention, generally obviates the need for the incorporation of mechanical fluid direction systems, e.g., microfabricated pumps, valves and the like, within the device itself, or for external fluid movement systems which rely upon pressure flow of materials, e.g., pneumatic systems. Effectively, such systems provide virtual pumps and valves for fluid transport and direction, which pumps and valves have no moving parts.

The number of ports at which voltage may be simultaneously controlled will generally depend upon the complexity of the operation to be performed by the device. Typically, the devices of the invention will include at least three ports at which the voltage is simultaneously controlled, preferably, at least four, more preferably at least five, and in some embodiments will employ six or more ports where the voltage is simultaneously controlled.

Figure 2:
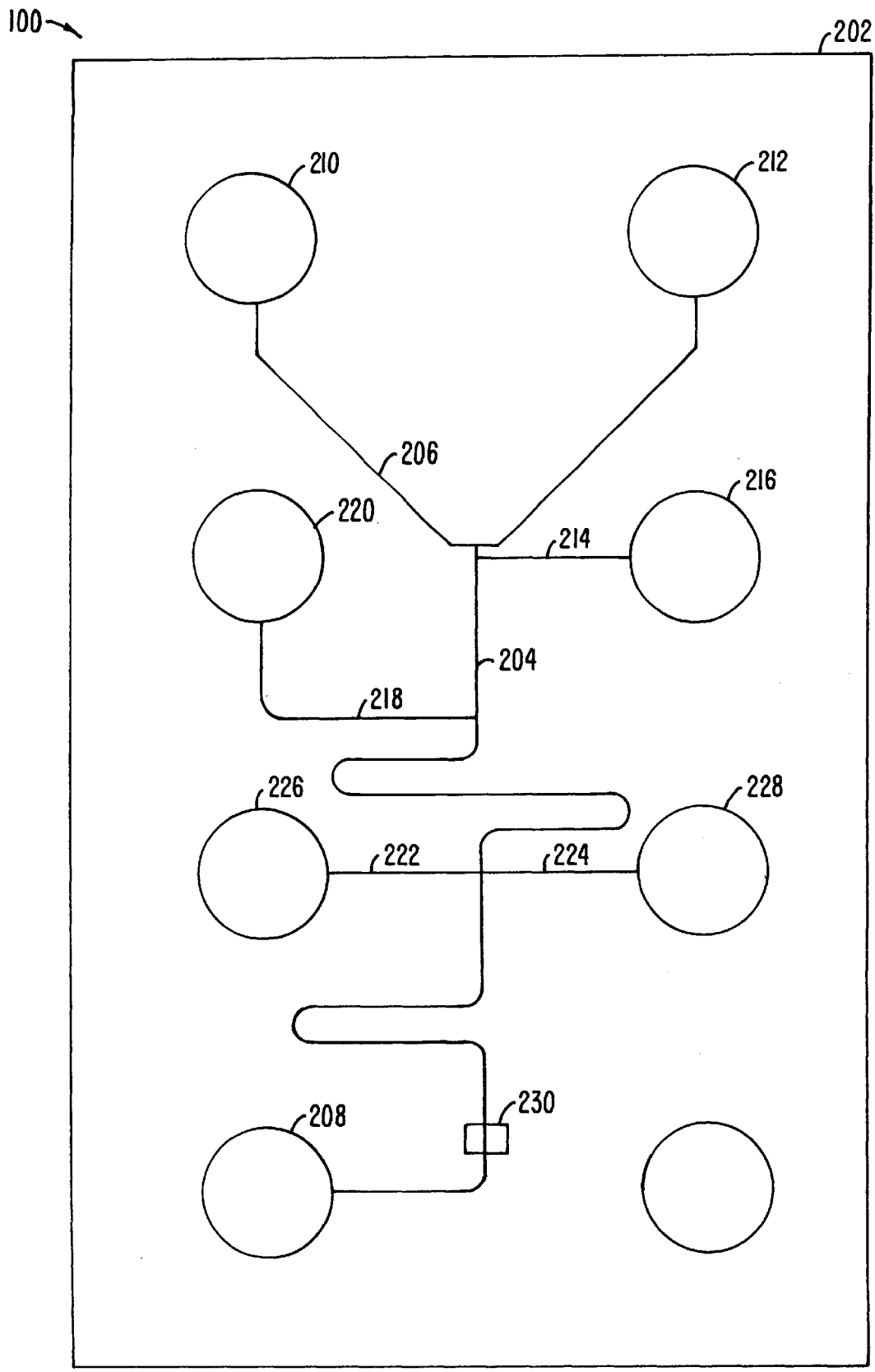
FIG. 2 is a schematic illustration of one embodiment of a microfluidic device of the present invention.

FIG. 2 is an illustration of a microfluidic device according to the present invention. As shown, the device 100, comprises a body, which is entirely or substantially fabricated from a polymeric material. The body includes a plurality of interconnected channels disposed in it, for the transport and direction of fluids.

As shown in FIG. 2, the device 100 is fabricated from a planar substrate 202, which has the various channels fabricated into its surface. A second planar layer overlays the first and includes holes disposed through it to form the various reservoirs (cover layer not shown). These reservoirs also serve as the ports at which the various electrodes are placed into electrical contact with fluids in the system. This second planar element is then bonded to the first.

The device illustrated, includes a main fluid channel 204 which runs longitudinally down the central portion of the substrate 202. The main channel 204 originates in and is in fluid communication with buffer channel 206, and terminates, and is in fluid communication with waste reservoirs 208. Buffer channel 206 is in fluid communication with two buffer reservoirs 210 and 212. The device is shown having a number of channels intersecting the main channel 204. For example, buffer channel 214 terminates in, and is in fluid communication with main channel 204 near its originating point, and is at its other terminus, in fluid communication with buffer reservoir 216. Sample introduction channel 218 also terminates in and is in fluid communication with main channel 204, and is, at its other terminus, in fluid communication with sample reservoir 220. Additional buffer/waste channels 222 and 224, and buffer/waste reservoirs 226 and 228 are also shown. A detection window 230, i.e., for detecting the transit of fluorescent or other dyes is also shown. The descriptors for the various wells and channels are primarily offered for purposes of distinguishing the various channels and wells from each other. It will be appreciated that the various wells and channels can be used for a variety of different reagents, depending upon the analysis to be performed.

Application of an electroosmotic flow system into the device shown involves placing electrodes into electrical contact with each of the various reservoirs. By modulating the voltages applied at each of these electrodes, e.g., applying voltage gradients across selected flow/current paths, one can selectively control and direct fluid flow/material transport within the device, as described above. In some aspects, the fluid control system may include optional sensor channels (not shown), for monitoring the voltage at the various intersections.

Although illustrated in terms of a seven reservoir microfluidic device, electroosmotic fluid direction systems can be readily employed in the transport and direction of materials in more complex channel structures for performing a variety of specific manipulations, analyses, preparations, and the like. Examples of such channel structures are described in copending, commonly owned U.S. application Ser. No. 08/761,575, filed Dec. 6, 1996, and incorporated herein by reference in its entirety for all purposes.

V. Applications

The microfluidic devices and systems of the present invention are capable of broad application and may generally be used in the performance of chemical and biochemical synthesis, analysis and detection methods. Generally, the devices of the invention can replace conventional laboratory equipment and methods, including measuring and dispensing equipment, as well as more complex analytical equipment, e.g., HPLC, SDS-PAGE, and immunoassay systems.

For example, these devices may be employed in research, diagnostics, environmental assessment and the like. In particular, these devices, with their micron and submicron scales, volumetric fluid control systems, and integratability, may generally be designed to perform a variety of chemical and biochemical operations where these traits are desirable or even required. In addition, these devices may be used in performing a large number of specific assays that are routinely performed at a much larger scale and at a much greater cost, e.g., immunoassays.

The devices may also be used to carry out specific operations in the analysis or synthesis of a sample. For example, the devices may include reaction chambers for performing synthesis, amplification or extension reactions. The devices may similarly include sample analysis elements for the detection of a particular characteristic of the sample, such as a capillary channel for performing electrophoresis on the sample. In such cases, and as described previously, devices for use in such detection methods will generally include a transparent detection window for optical or visual detection.

Examples of some more specific applications of these devices are set forth in, e.g., U.S. patent application Ser. No. 08/761,575, previously incorporated herein by reference, and commonly assigned U.S. patent application Ser. No. 60/086,240, filed Apr. 4, 1997 (Attorney Docket No. 17646-000300), also incorporated herein by reference in its entirety.

EXAMPLES

Example 1

Fluid Direction in a Polymethylmethacrylate Substrate (PMMA)

Microfluidic devices were fabricated in polymethylmethacrylate (PMMA) using various methods, including: (1) casting a polymer precursor against the inverted replica of the channel geometry; and (2) embossing a solid sheet of PMMA against the inverted replica by applying suitable temperature and pressure.

An inverted replica of a microfluidic device having the channel geometry shown in FIG. 2, was fabricated from silicon using inverted lithography, i.e., etching away the surface everywhere except where the channels were to be located. This was done with an anisotropic etch (hot KOH) so that the sidewalls of the raised channels were planes at an angle of 55°. The resulting raised channels were 10.87 $\mu$m high.

A polymethylmethacrylate polymer was cast against the above-described silicon mold, and this casting was bonded to another planar piece of PMMA which had holes drilled through it to provide the sample and reagent wells. Bonding was carried out by applying pressure and temperature of 98° C. The resulting device was used for subsequent analysis.

In order to demonstrate the ability to switch electroosmotic flow in a PMMA device, and to measure the magnitude of that flow, the above described device was filled with 100 mM borate buffer, at pH 7. A neutral marker, Rhodamine B, diluted in running buffer, was aliquoted into reservoir 226 (as referenced in FIG. 2). The neutral marker is fluorescent to allow for its detection, and uncharged, so that it will move with the flow of buffer, and thus indicate electroosmotic flow of the buffer, rather than electrophoretic mobility of the marker.

The running protocol flowed the rhodamine dye from reservoir 226 to reservoir 228, across the intersection of channels 222/224 and channel 204 (injection point) prior to injection. Sample flow was detected, not at detection window 230, but instead, at a point in the main channel 3.25 mm from the injection point, before the channel turns towards reservoir 216.

Detection of rhodamine was carried out using a Nikon inverted Microscope Diaphot 200, with a Nikon P101 photometer controller, for epifluorescent detection. An Opti-Quip 1200–1500 50W tungsten/halogen lamp coupled through a 10× microscope objective provided the light source. Excitation and emission wavelengths were selected with a DAPI filter cube (Chroma, Brattleboro Vt.) fitted with an appropriate filter.

Figure 3:
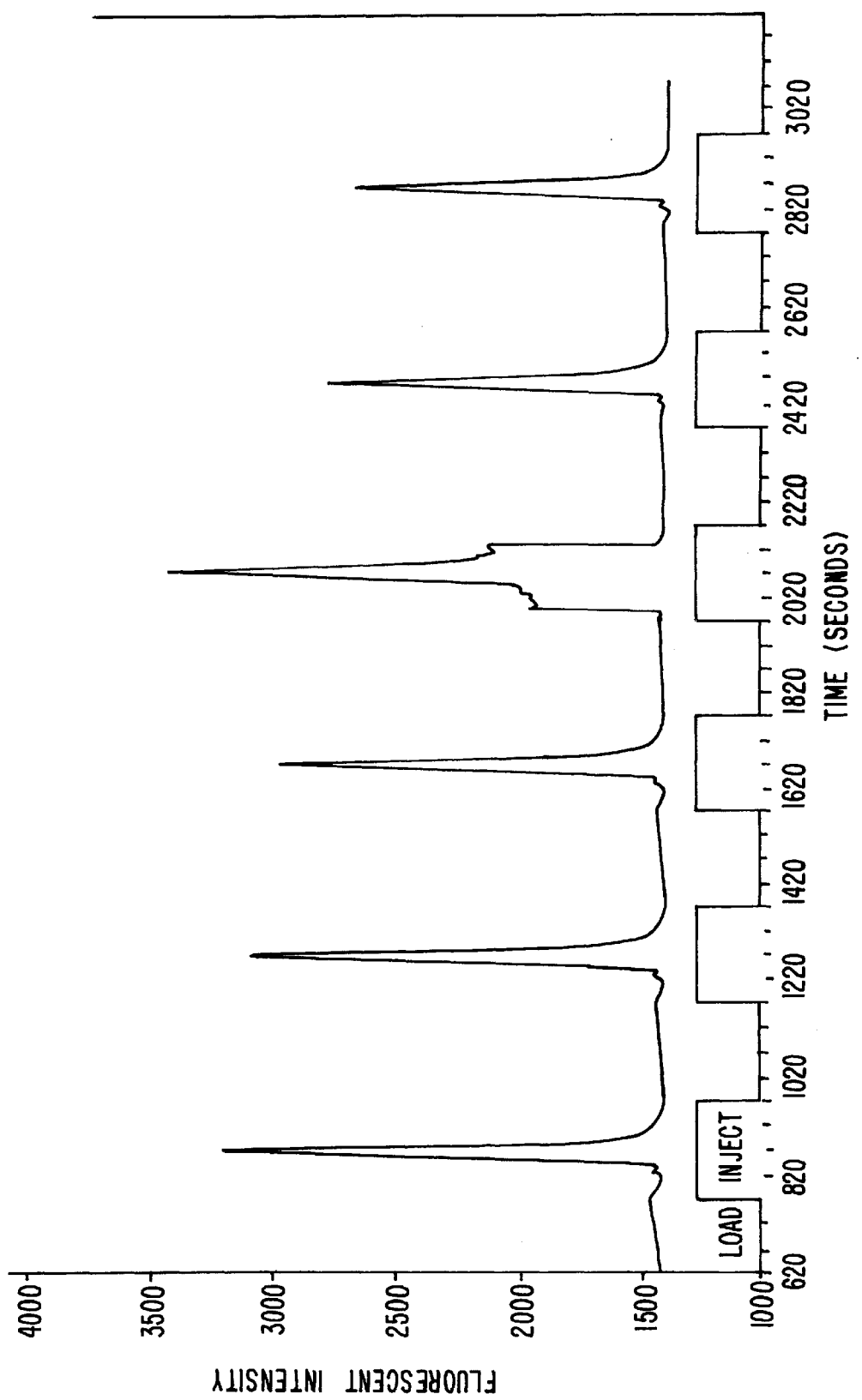
FIG. 3 is a plot illustrating electroosmotic transport of a neutral fluorescent dye past a detector in a microfluidic channel, fabricated in a polymeric substrate.

In this experiment, the total path length between reservoirs 208 and 216, along which the running voltage was applied, was 52 mm. The voltage applied along this channel was 1200 V, yielding an electric field of 235 V/cm. Rhodamine B sample plugs at the injection point were injected at 400 second intervals. A plot of fluorescent intensity detected at the detection point vs. time is shown in FIG. 3.

The time needed for the sample to travel the 3.25 mm from the injection point to the detection point was 85 seconds, translating to a velocity of $3.8 \times 10^{-3}$ cm/s. It was therefor concluded that the electroosmotic mobility of the buffer under these conditions was $1.6 \times 10^{-5}$ cm$^2$/Vs.

Example 2

Electroosmotic Flow in Injection Molded PMMA Substrate

A similar experiment to that described above, was performed in a microfluidic device having a single channel connecting two reservoirs or wells. In this experiment, the device was fabricated by injection molding the first planar substrate using PMMA (Acrylite M30), which defined the channel of the device, and bonding a drilled second planar PMMA substrate to seal the channels and provide the reservoirs. Again, bonding was done with pressure at elevated temperatures, e.g., 85° C. and 2–5 kg pressure.

The channel and reservoirs of the device were filled with 10 mm sodium borate running buffer, at pH 8.0, and Rhodamine was additionally placed in one reservoir. 2000V were applied to the rhodamine containing reservoir with 1500V applied to the other reservoir. This yielded an applied voltage of 500V along the channel connecting the two wells. Detection was carried out at a point in the channel, 2.2 cm from the rhodamine containing reservoir. Transit time for the dye from its reservoir to the detection point was 187 seconds and 182 seconds in duplicate runs, yielding an average $\mu$EO of $5.25 \times 10^{-5}$ $cm^2V^{-1}s^{-1}$.

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

We claim:

1. A microfluidic device, comprising:
   a body comprising a substantially polymeric substrate layer and a cover layer, the substantially polymeric substrate layer comprising at least two intersecting microchannels embossed therein, the cover disposed over at least a portion of the at least two intersecting microchannels.

2. The microfluidic device of claim 1, wherein the cover layer is laminated to the substantially polymeric substrate layer.

3. The microfluidic device of claim 2, wherein the cover layer and the substantially polymeric substrate layer are fused.

4. The microfluidic device of claim 1, wherein the cover layer is laminated to the substantially polymeric substrate layer by one or more of adhesive bonding, sonic welding, pressure bonding, thermal bonding and thermal bonding under pressure.

5. The microfluidic device of claim 1, wherein the cover layer is substantially fabricated from glass, or a polymer, or a combination thereof.

6. The microfluidic device of claim 1, wherein the microchannels are embossed as grooves in a substantially planar portion of the substantially polymeric substrate layer, which cover layer overlays the grooves, thereby forming a closed microchannel.

7. The microfluidic device of claim 1, wherein the channels have a surface potential associated therewith.

8. The microfluidic device of claim 1, wherein the at least two channels support electroosmotic flow of fluidic material in the channels.

9. The microfluidic device of claim 1, wherein the at least two channels have a zeta potential associated therewith which supports an electroosmotic flow of at least about $5 \times 10^{-4}$ $cm^{-2}v^{-1}s^{-1}$ for a 5 mM sodium borate buffer at pH 7 when said buffer is disposed within the channels.

10. The microfluidic device of claim 1, wherein the at least two channels have a zeta potential associated therewith which supports an electroosmotic flow of at least about $1 \times 10^{-5}$ $cm^{-2}v^{-1}s^{-1}$ for a 5 mM sodium borate buffer at pH 7 when said buffer is disposed within the channels.

11. The microfluidic device of claim 1, wherein the at least two channels have a zeta potential associated therewith which supports an electroosmotic flow of at least about $1 \times 10^{-5}$ $cm^{-2}v^{-1}s^{-1}$ for a sodium borate buffer between about 1 and about 100 mM at a pH of about 6 to about 9 when said buffer is disposed within the channels.

12. The microfluidic device of claim 1, wherein the at least two channels have a zeta potential associated therewith which supports an electroosmotic flow of at least about $2 \times 10^{-5}$ $cm^{-2}v^{-1}s^{-1}$ for a sodium borate buffer between about 1 and about 100 mM at a pH of about 6 to about 9 when said buffer is disposed within the channels.

13. The microfluidic device of claim 1, wherein the at least two channels have a zeta potential associated therewith which supports an electroosmotic flow of at least about $1 \times 10^{-4}$ $cm^{-2}v^{-1}s^{-1}$ for a sodium borate buffer between about 1 and about 100 mM at a pH of about 6 to about 9 when said buffer is disposed within the channels.

14. The microfluidic device of claim 1, wherein at least one of the at least two microchannels comprises at least one cross-sectional dimension in the range of from about 0.1 micron to about 500 microns.

15. The microfluidic device of claim 1, the device further comprising a plurality of ports proximal to the channels, the ports each optionally comprising one or more electrode disposed therein.

16. The microfluidic device of claim 15, comprising at least four ports, each proximal to a terminal region of at least one of the at least two microchannels, each port optionally comprising at least one electrode disposed therein.

17. The microfluidic device of claim 16, the device comprising at least four electrodes, with at least one electrode being disposed in each of the at least four ports, the device further comprising an electrical controller for concomitantly applying an electrical potential to each of the four electrodes.

18. The device of claim 17, wherein the electrical controller comprises a voltage controller.

19. The device of claim 18, further comprising a computer operably linked to the voltage controller, wherein the computer is programmed to regulate electrical potential of the electrodes.

20. The microfluidic device of claim 1, further comprising fluid disposed within the at least one microchannel.

21. The microfluidic device of claim 1, the substantially polymeric substrate comprising at least 60% polymer.

22. The microfluidic device of claim 1, wherein the substantially polymeric substrate layer is fabricated from a material which is selected from: a rigid material, a semi-rigid material, an opaque material, a semi-opaque material, and a transparent material.

23. The microfluidic device of claim 1, wherein the substantially polymeric substrate layer comprises one or more of: a polydimethylsiloxane (PDMS), polymethylmethacrylate (PMMA), polyurethane, polyvinylchloride (PVA), polystyrene, polysulfone, and polycarbonate.

24. The microfluidic device of claim 1, wherein the cover layer comprises a quartz window.

25. The device of claim 1, wherein the cover layer and the substantially polymeric substrate layer are substantially planar.

26. The device of claim 1, the device further comprising a surface coating on the substantially polymeric substrate or on the cover layer, which coating, when present, modifies the zeta potential of the polymeric substrate, or the cover layer, thereby modifying the zeta potential in at least one of the at least two microchannels.

27. A device for fabrication of a polymeric substrate, the device comprising: a mold for embossing the surface of a substantially polymeric substrate with a microchannel network, the mold comprising an embossing surface comprising a network of intersecting raised or lowered regions for embossing at least two intersecting grooves in the polymeric substrate, wherein the intersecting grooves embossed in the substantially polymeric substrate by the embossing surface have at least one dimension between about 0.1 and about 500 microns.

28. The device of claim 27, wherein the embossing surface is a stamp, or, a rolling press.

29. The device of claim 27, further comprising a polymeric substrate in contact with the mold.

30. The device of claim 29, wherein the polymeric substrate is a region of a polymer sheet.

31. The device of claim 27, the embossing surface further comprising an additional raised or lowered region corresponding to a well, groove, chamber, reservoir or additional channel region.

* * * * *

UNITED STATES PATENT AND TRADEMARK OFFICE
CERTIFICATE OF CORRECTION

PATENT NO. : 6,238,538 B1
DATED : May 29, 2001
INVENTOR(S) : J. Wallace Parce et al.

It is certified that error appears in the above-identified patent and that said Letters Patent is hereby corrected as shown below:

<u>Column 16,</u>
Line 53, "PVA" should be -- PVC --.

Signed and Sealed this

First Day of April, 2003

JAMES E. ROGAN
*Director of the United States Patent and Trademark Office*